US008465770B2

(12) United States Patent
Annemarie Jansen et al.

(10) Patent No.: US 8,465,770 B2
(45) Date of Patent: Jun. 18, 2013

(54) LOW DOSE CONTROLLED RELEASE TABLET

(75) Inventors: Korinde Annemarie Jansen, Beuningen (NL); Dirk Pamperin, Nijmegen (NL)

(73) Assignee: Synthon BV, Nijmegen (NL)

( * ) Notice: Subject to any disclaimer, the term of this patent is extended or adjusted under 35 U.S.C. 154(b) by 504 days.

(21) Appl. No.: 12/634,890

(22) Filed: Dec. 10, 2009

(65) Prior Publication Data

US 2010/0092552 A1      Apr. 15, 2010

Related U.S. Application Data

(60) Provisional application No. 61/140,712, filed on Dec. 24, 2008.

(51) Int. Cl.
*A61K 9/24* (2006.01)

(52) U.S. Cl.
USPC ........... 424/472; 424/474; 424/464; 424/465; 424/486

(58) Field of Classification Search
USPC .......................... 424/472, 474, 464, 465, 486
See application file for complete search history.

(56) References Cited

U.S. PATENT DOCUMENTS

| | | | |
|---|---|---|---|
| 4,217,305 A | 8/1980 | Imai et al. | |
| 4,703,063 A | 10/1987 | Imai et al. | |
| 4,731,478 A | 3/1988 | Niigata et al. | |
| 4,772,475 A | 9/1988 | Fukui et al. | |
| 4,868,216 A | 9/1989 | Imai et al. | |
| 4,895,841 A | 1/1990 | Sugimoto et al. | |
| 4,966,768 A | 10/1990 | Michelucci et al. | |
| 6,177,430 B1 | 1/2001 | Thompson et al. | |
| 6,287,599 B1 | 9/2001 | Burnside et al. | |
| 6,335,467 B1 | 1/2002 | Englert et al. | |
| 6,368,628 B1 | 4/2002 | Seth | |
| 6,436,441 B1 | 8/2002 | Sako et al. | |
| 6,528,685 B2 | 3/2003 | Cohen et al. | |
| 6,835,853 B2 | 12/2004 | Hoorn et al. | |
| 6,965,051 B2 | 11/2005 | Hoorn et al. | |
| 7,018,658 B2 | 3/2006 | Platteeuw | |
| 2003/0147955 A1 | 8/2003 | Platteeuw et al. | |
| 2003/0180352 A1* | 9/2003 | Patel et al. | 424/465 |
| 2004/0096502 A1 | 5/2004 | Platteeuw | |
| 2005/0100602 A1* | 5/2005 | Sako et al. | 424/468 |
| 2005/0100603 A1* | 5/2005 | Sako et al. | 424/468 |

FOREIGN PATENT DOCUMENTS

| | | |
|---|---|---|
| EP | 0 034 432 B1 | 8/1981 |
| EP | 0 257 787 B1 | 3/1988 |
| EP | 0 309 157 A1 | 3/1989 |
| EP | 0 194 838 B1 | 9/1993 |
| EP | 0 533 297 | 11/1997 |
| WO | WO 94/06414 | 3/1994 |
| WO | WO 00/27364 | 5/2000 |
| WO | WO2007/049916 * | 5/2007 |
| WO | WO 2007/131804 | 11/2007 |

OTHER PUBLICATIONS

NDA 20-579 FDA Office of Clinical Pharmacology and Biopharmaceutics Review, pp. 1-6, 1997.
Flowmax, MIMMS Abbreviated Prescribing Information, MIMMS Australia, 1996-2002.
Presentation entitled: "In Vivo" Performance of Hydrophilic Matrix Tablets Utilizing HPMC: Case Studies by Tim D. Cabelka, Ph.D. and Thomas D. Reynolds, Ph.D., The Dow Chemical Company, Oct. 17, 2000.
FDA—FOIA Labeling Information for Flomax®, 2001.
Dunn CJ, Matheson A and Faulds DM. "Tamsulosin A review of its pharmacology and therapeutic efficacy in the management of lower urinary tract symptoms." *Drugs Aging* 2002; 19; 135-161.
Dutkiewics S. "Efficacy and tolerability of drugs for treatment of benign prostatic hyperphasia." *Int Urology and Nephrology* 2001; 32; 423-432.
Harada K. and Fujimara A. "Clinical pharmacology of 1-A selective and nonselective 1-blockers." *BJU International* 2000; 86; 31-35.
Lyseng-Williamson KA, Jarvis B and Wagstaff AJ. "Tamsulosin an update of its role in the management of lower urinary tract symptoms." *Drugs* 2002; 62; 135-167.
Michel MC, Neumann HG, Mehlburger L, Schumacher H and Goepel M. "Does the time for administration (morning or evening affect the tolerability or efficacy of tamsulosin?" *BJU International* 2001; 87; 31-34.
Soeishi Y, Korobi M, Kobayashi SI and Higuchi S. "Sensitive method for the determination of tamsulosin in human plasma using high-performance liquid chromotography with fluorescence detection" *J of Chromotography* 1990; 553; 291-296.
Taguchi K. Schafers RF and Michel MC. "Radioreceptor assay analysis of tamsulosin and terazosin pharmacokinetics." *Br J Clin Pharmacol.* 1998; 45; 49-55.
Van Hoogdalem EJ, Soeishi Y, Matsushima H and Higuchi S. "Disposition of the selective adrenoceptor antagonist tamsulosin in humans: Comparison with data from interspecies scaling." *J Pharm Sciences* 1997; 86; 1156-1161.
Rabasseda and Fitzpatrick, "Tamsulosin: The First Prostate-Selective alpha 1a-Adrenoceptor Antagonist for Treatment of Symptomatic Benign Prostatic Hyperplasia," Drugs of Today, vol. 32, No. 3, 1996, pp. 259-268.

* cited by examiner

*Primary Examiner* — Fereydoun G Sajjadi
*Assistant Examiner* — Danielle Sullivan
(74) *Attorney, Agent, or Firm* — Mark R. Buscher

(57) ABSTRACT

Low dose pharmaceuticals can be delivered for a prolonged period using a tablet-in-tablet design wherein the drug is contained in a controlled release matrix in the outer compression coating layer but not in the inner tablet core.

22 Claims, No Drawings

LOW DOSE CONTROLLED RELEASE TABLET

This application claims the benefit of priority under 35 U.S.C. §119(e) from U.S. Provisional Application Ser. No. 61/140,712, filed Dec. 24, 2008, the entire contents of which are incorporated herein by reference.

BACKGROUND OF THE INVENTION

Tamsulosin is a known chemical compound having alpha-adrenergic blocking activity that is useful for treatment of cardiac insufficiencies and benign prostatic hyperplasia (BPH). Tamsulosin is the common name for (R)-5-[2-[[2-(2-ethoxyphenoxy)ethyl]amino]propyl]-2-methoxy-benzenesulfonamide. It is disclosed in EP 34432 and U.S. Pat. No. 4,731,478. Tamsulosin is a potent pharmaceutically active agent and is typically administered in amounts of less than 1 mg per day, usually 0.4 mg.

Several medicaments comprising tamsulosin, specifically tamsulosin hydrochloride, are currently marketed. The first commercially available medicament comprising tamsulosin (OMNIC, FLOMAX, marketed since 1993) were gelatin capsules filled with pellets comprising tamsulosin (0.4 mg strength). In Japan, an orally-disintegrating tablet based on WOWTAB technology (Harnal D), is also on the market.

Recently a controlled release tablet formulation was introduced on the market in Europe (Omnic OCAS, Mapelor OCAS) also containing 0.4 mg of tamsulosin hydrochloride. The tablet is purported to have less or no food effect in comparison to the capsule formulations. This marketed tablet medicament uses the so called OCAS drug delivery system which enables gradual release of a drug as the tablet travels through the digestive tract, including the colon. It appears that the relevant patent covering the OCAS delivery system is a patent family based on WO 94/06414 (EP 661045, U.S. Pat. No. 6,436,441).

In general, the OCAS system comprises a drug, a hydrogel-forming polymer and a highly water soluble hydrophilic additive (a "hydrophilic base"), which is important in aiding rapid water penetration into the core. The concept is that the preparation absorbs water as it enters and passes through the upper digestive tract such that the water-swellable polymer undergoes substantially complete gelation (i.e. at least 70%). As the preparation continues down the digestive tract, its gelled surface continues to constantly erode, thereby maintaining a release of the drug even in the lower digestive tract, e.g., in the colon.

The stability and the rate of formation of the gel layer, as well as the rate of its erosion after prolonged hydration are important factors in designing an OCAS tablet. Too little hydrophilic base can lead to insufficient gelation such that release in the colon is compromised. Too much hydrophilic base can result in a gel that is too fragile and releases the drug too rapidly and hence also compromises release in the colon. In addition to these gelation/viscosity issues, the hydrogel-forming polymer should also preferably be selected so as to provide sufficient mechanical strength so that the tablet can essentially retain its shape during its travel in spite of the contractile forces of the digestive tract.

In view of the above, the hydrogel-forming polymer which can be used in the OCAS system as the matrix-forming agent is preferably a polymer showing a high viscosity on gelation, e.g., a viscosity of not less than 1000 cps in 1% aqueous solution (at 25° C.). Because viscosity of the gel depends in part on the molecular weight, the hydrogel-forming polymer is preferably a substance having a high molecular weight of not less than 2 million and more preferably of not less than 4 million. A preferred hydrogel-forming polymer according to U.S. Pat. No. 6,436,441 is a poly(ethylene oxide), especially one having a molecular weight of not less than 2 million.

The actually marketed OCAS tablet comprising tamsulosin (or "TOCAS" tablet) comprises a high molecular weight poly(ethylene oxide) as the hydrogel-forming polymer and a polyethylene glycol as the solubility enhancing hydrophilic base. The TOCAS tablets are film coated, which coating contains hydroxypropylmethyl cellulose.

WO 2004/078212 teaches that manufacturing a tablet based on poly(ethylene oxide) with a molecular weight of 2,000,000 or higher as taught in U.S. Pat. No. 6,436,441, is difficult. For instance, the polymer becomes very sticky when exposed to moisture. Additionally, granulating the polymer turned out to be problematic. And because the intended/preferred drug, tamsulosin hydrochloride, is used in low doses, the patent publication teaches that direct compression and dry granulation are unsuited because of content uniformity concerns; e.g., the drug concentration may not be uniform throughout the tabletting blend which leads to variable dosage strengths. To address these manufacturing issues, WO 2004/078212 proposes "sizing" particles of poly(ethylene oxide) by spraying an aqueous solution or suspension of a sizing agent onto the particles and drying the particles. The sizing agent is typically a portion of the polyethylene glycol used as the hydrophilic base. Generally the drug, which is preferably tamsulosin HCl, is included in the aqueous solution/suspension of the sizing agent. The resulting poly(ethylene oxide)-containing granulate is purported to be readily incorporated into a finished dosage form such as a tablet by conventional techniques.

Another proposal for the delivery of tamsulosin throughout the whole digestive tract from a tablet formulation was disclosed in WO 2007/131804. The composition comprises a) 0.1 to 1 weight % of tamsulosin, preferably tamsulosin hydrochloride; b) 40-80 weight % of a water-swellable matrix-forming composition comprising (i) a pH-sensitive swellable hydrophilic polymer, which is a cross-linked polyacrylic acid polymer and preferably it is carbomer, and (ii) a pH-insensitive swellable hydrophilic polymer, which preferably is a linear polymer such as hydroxypropyl methylcellulose (HPMC), especially a high molecular weight HPMC; and c) optionally a water insoluble binder.

While the tablets of WO 2007/131804 exhibit a good release profile of tamsulosin, the tablet design (composition, size, shape, etc.) again requires a careful balance of properties; and achieving sufficient release in the colon is often problematic for this kind of controlled release tablet.

Obtaining controlled release throughout the digestive tract, including consistent release in the water-reduced colon, can be challenging. Obtaining such release with a low dose drug further complicates the matter as shown in the above tamsulosin tablets. It would be desirable to find a robust, easy-to-design tablet for providing low dose drugs such as tamsulosin with good drug release throughout the whole digestive tract including the colon.

SUMMARY OF THE INVENTION

The present invention is based on the idea of using a tablet-in-tablet design to deliver low dose drugs in a controlled release fashion, wherein the inner tablet core is drug-free (or essentially drug-free) while the outer compression coating contains the drug in a controlled release matrix. Such a tablet design can provide controlled release tablets, such as tamsulosin tablets, that can be manufactured in a suitable size and shape for oral administration and can offer greater design flexibility in the matrix type and composition for achieving the desired controlled release profile.

Accordingly, a first aspect of the invention relates to a controlled release pharmaceutical tablet comprising (a) an inner tablet core comprising at least one pharmaceutically acceptable excipient but substantially free from any pharmaceutically active agent; and (b) an outer compression coating layer surrounding the inner tablet core and which comprises a controlled release matrix having a pharmaceutically active agent dispersed therein; wherein the total amount of pharmaceutically active agent contained in the tablet is within the range of 0.1 to 5 mg. Typical pharmaceutical active agents include tamsulosin, tolterodine, and pharmaceutically acceptable salts of each.

A more specific aspect of the invention relates to a controlled release tamsulosin tablet, which comprises: (a) an inner tablet core comprising at least one pharmaceutically acceptable excipient and substantially free from any pharmaceutically active agent; and (b) an outer compression coating layer surrounding said inner tablet core and which comprises 0.1 to 2 mg of tamsulosin or salt thereof, typically tamsulosin hydrochloride, dispersed in a water-swellable matrix comprising (i) at least one pH-sensitive swellable hydrophilic polymer, which is a cross-linked polyacrylic acid polymer, (ii) at least one pH-insensitive swellable hydrophilic polymer; and optionally (iii) a water insoluble binder. Typically the pH-sensitive polymer is a carbomer and the pH-insensitive polymer preferably is a linear polymer such as hydroxypropyl methylcellulose (HPMC), especially a high molecular weight HPMC. In some embodiments it is desirable that the inner tablet core contain a water-swellable matrix composition, even though it does not contain any drug substance, which is further preferably the same as the water-swellable matrix composition used in the outer compression coating layer.

DETAILED DESCRIPTION OF THE INVENTION

The present invention relates to a tablet for delivering low dose drugs in a controlled release fashion. The tablet is a tablet-in-tablet design wherein the drug is contained essentially in a controlled release outer compression coating layer but not in the inner tablet core. This design can facilitate the formation of tablets of low dose drugs that exhibit the desired release profiles, especially prolonged release through the colon, and that are elegant pharmaceutical oral dosage forms.

A "tablet-in-tablet" design means that the dosage form comprises an inner tablet that is covered and surrounded by an outer coat that is compressed onto the inner tablet. Both inner and outer parts are made by a compression process that is characteristic for making tablets, hence the "tablet-in-tablet" expression. Tablet presses allowing such a technique are known as alternate tablet presses or "tablet-in tablet" presses and are known in the art.

In general the controlled release tablet of the invention can contain any pharmaceutically active agent or "drug" that is used in low amounts per unit dose; e.g., less than 5 mg, typically 0.1 to 2.0 mg, preferably 0.1-1.0 mg. The tablet is most advantageous for a low dose drug that is delivered over a long time, e.g., a dissolution profile wherein 95% release is achieved in not less than 12 hours, more typically not less than 14 hours, and in some preferred embodiments not less than 16 hours, in an appropriate, FDA-acceptable, dissolution test. The preferred active is tamsulosin or a pharmaceutically acceptable salt thereof such as tamsulosin hydrochloride. Each tablet contains from 0.1 to 1 mg, preferably 0.2, 0.4 or 0.8 mg, of tamsulosin, expressed as tamsulosin hydrochloride. Other useful drugs include tolterodine and pharmaceutically acceptable salts thereof such as tolterodine tartrate in doses of 2 or 4 mg.

The pharmaceutically active agent is contained in the outer compression coating layer. The outer compression coating layer comprises a controlled release matrix having the drug dispersed therein. Matrix-based release technologies are well known in the art and generally rely on diffusion of drug out of the matrix and/or liberation via erosion of the matrix. In principle, the matrix could be based on a lipophilic matrix or hydrophilic matrix.

Generally the controlled release matrix used in the present invention is a water-swellable matrix, and preferably is one comprised of a pH-sensitive polymer and a pH-insensitive polymer. Such a mixture of polymers as a matrix was described in the above-mentioned WO 2007/131804. The use of such a matrix system provides all of the advantages as set forth in WO 2007/131804 and, because of the design of the present tablet, the tablet may offer improved release in the colon over the tablets of WO 2007/131804. For example, the tablet-in-tablet design of the present invention effectively decreases the amount of the matrix that needs to undergo gellation in order to release drug and allows the fine tuning of a slow and regular release of the drug from the gel layer. Thus, the overall gellation index of the tablet of the present invention can be made to be very similar to the marketed TOCAS composition.

The water-swellable matrix-forming composition comprises at least 30%, typically 40% to 80%, and often 50-70%, of the outer compression coating layer (note that all percentages used herein refer to weight percent unless otherwise indicated). As noted above, the matrix composition preferably comprises two types of matrix-forming polymers.

The first matrix-forming component of the matrix-forming composition is a pH-sensitive swellable hydrophilic polymer, i.e. a polymer that swells in water and produces hydrogels in a rate and amount that is dependent on the environmental pH-range. The pH-sensitive swellable hydrophilic polymer is preferably a cross-linked polyacrylic acid polymer. The most preferred such polymer in the compositions of the present invention is a carbomer. Carbomers are synthetic high-molecular-weight polymers of acrylic acid that are crosslinked with either allyl sucrose or with allyl ethers of pentaerythritol. They contain from 56 to 68% of carboxylic acid groups, when calculated on a dry basis. Their molecular mass cannot be directly evaluated due to the presence of the crosslinker, but is estimated from 700,000 to 4 billion. Carbomers disperse (do not dissolve) in water to form acidic colloidal solutions of low viscosity, however, when neutralized at above the pK value (approximately at pH >5.5), they produce highly viscous gels.

Within a tablet and in an aqueous environment, the carbomer produces a hydrogel mass, often referred to as a hydrogel layer. Due to the crosslinking, the gel does not erode in the gastrointestinal tract (as is common in the case of gels formed from hydrophilic linear polymers) and releases the drug mainly by a diffusion mechanism.

The pharmaceutically acceptable types of carbomer polymers differ from each other by the type of cross linker, percentage of the crosslinker, and residual solvents used for polymerization. While the Ph. Eur. has a single monograph for the whole class of carbomers, the USP has several monographs. The most preferred types of carbomers in compositions of the invention are those having an extra low content of residual polymerization solvent, because of the intended use in oral preparations. In general, such suitable carbomers are marketed with a letter P after its name. Furthermore, it is preferred that the dynamic viscosity of the carbomer polymer measured in aqueous solution is sufficiently high (preferably at least 4000 mPa/s, measured at 0.5% aqueous solution); however the dynamic viscosity of carbomers in plain water is not a limiting factor in the compositions of the present invention.

Taking the above in consideration, various marketed carbomers, e.g., under the brand name Carbopol® (Noveon, Inc., Cleveland, Ohio, USA), are suitable for making the tablets of the present invention. These include Carbopol 934P, which is crosslinked with an allyl sucrose and is polymerized in benzene; and Carbopol 71G, Carbopol 974P and Carbopol 971P, which are crosslinked with an allyl pentaerythritol and polymerized in ethyl acetate. Carbopol 71G is a granulated form of Carbopol 971P.

Carbomers, in general, have good tabletting properties and good binding properties; therefore they are suitable for a variety of tabletting processes including those that do not use a liquid. The Carbopol 71 G is particularly useful in certain embodiments of the invention as it is a granulated product with good handling properties and readily tablettable by a direct compression process.

The relative amount of the pH-sensitive swellable polymer, and specifically the carbomer, is generally in the range of from 3% to 60%, more typically 3 to 25%, and in some embodiments 4 to 15%, of the matrix-forming composition. Alternatively or additionally, the amount of the pH-sensitive swellable polymer is generally in the range of 2% to 30%, more typically 3% to 15%, of the total weight of the outer compression coating layer.

The second matrix-forming component is a pH-insensitive swellable hydrophilic polymer, which is preferably a linear (i.e. not crosslinked) polymer. The pH-insensitive hydrophilic polymer can preferably produce a viscous gel and is at least swellable independently of the pH of the environmental fluid. If the polymer is linear, the gel of such polymer is water soluble and it releases the drug by a mechanism, which is different from that of the crosslinked polymer, that is mostly slow erosion and continual dissolution of the gel in the body fluid.

A preferred compound among the pH-insensitive swellable hydrophilic polymers is a hydroxypropyl methylcellulose (HPMC), particularly a high viscosity grade HPMC. The dynamic viscosity of HPMC can affect the overall release rate. In compositions of the invention, the HPMC brand should typically have a nominal dynamic viscosity of at least about 100,000 mPa/s (which actually means the actual viscosity range from about 80,000 to 120,000 mPa/s), when measured in a 2% (w/v) aqueous solution at 20° C. A preferred HPMC brand is Methocel K100 MCR (Dow Chemicals, USA).

Apart from the high viscosity HPMC, also pH-insensitive linear polyacrylates and polymethacrylates may be used, and accordingly any high molecular weight pH-insensitive polymer, and preferably a linear polymer, that may quickly form a viscous gel (e.g., hydroxypropylcellulose, hydroxyethylcellulose, etc.) can be used. Additional pH-insensitive swellable hydrophilic polymers (e.g. kollidon SR, polymethacrylates, etc) which are generally not gel forming but are merely swellable can also be used, but are somewhat less preferred than a gel forming polymer such as HPMC. Also a combination of two or more types and/or kinds of pH-insensitive polymers may be used to form the pH-insensitive swellable hydrophilic polymeric component of the water-swellable matrix-forming composition.

In respect to the tabletting process, care is generally taken that the pH-insensitive polymer should also have good tabletting properties (flowability, physical stability, etc.). It should preferably be non-hygroscopic and not be thermoplastic. Thus, for instance, in some embodiments poly(ethylene oxide) is preferably not used in the composition of the present invention as it could suffer from poor or difficult tabletting properties in a repeated, industrial-scale tabletting process. Nonetheless, such a polymer could be used in the invention generally and is not necessarily excluded.

The relative amount of the pH-insensitive swellable polymer, and specifically the HPMC, in the compositions of the present invention plays a role in the overall release rate and should be more than 40%, typically from 50% to 97%, more typically 60% to 95% of the matrix-forming composition. Alternatively or additionally, the amount of the pH-insensitive swellable polymer is generally from 25% to 80%, more typically 35% to 80% of the outer compression coating layer.

In a particular embodiment of the present invention, the matrix-forming composition comprises about 4 to 12%, especially 5-10%, of a carbomer and about 96 to 88%, especially 95-90%, of an HPMC.

While not strictly required, the presence of a water insoluble binder in the outer compression coating layer composition is generally advantageous. Water insoluble binders are well known in the art. A suitable binder is microcrystalline cellulose (or "MCC") as it also aids in achieving good content uniformity of the blend used to make the outer compression coating layer, even in the case of such a small amount of the active substance as in the present tamsulosin tablets. The amount of the binder generally does not exceed 60% and typically is from 5 to 50%, more typically 20 to 40%, of the outer compression coating layer composition.

The outer compression coating layer may contain other excipients as well. In particular, these excipients are added to improve the flowing properties (e.g., glidants such as talc, colloidal silicone dioxide, etc.) and/or to minimize the stickiness to tablet punches (lubricants such as magnesium stearate, calcium stearate, glyceryl behenate, etc.). Non-functional excipients such as microbial preservatives, colorants, flavorants, etc., can also be used in the composition. In general, their amounts are very low and do not affect the release rate. It should be noted that solubility-enhancing agents, i.e. highly water soluble compounds such as mannitol, lactose, polyethyleneglycol, etc., are not necessary in the compositions of the present invention and preferably are avoided from the tablet composition. Their presence would generally negatively affect the release rate during the first two hours of release.

The outer compression coating layer may be further coated if desired. For example, a tablet may be film-coated to improve its appearance and/or handling, using conventional film-coating materials and techniques. Such a film-coat does not substantially affect the release rate. Also, the weight of such a cosmetic coating, if present, is not included in the overall or total mass of the tablet for purposes of calculating the above-mentioned component percentages. Enteric coating of the tablets is, in essence, not necessary and is generally omitted.

The outer compression coating layer surrounds a tablet core. The tablet core comprises at least one pharmaceutically acceptable excipient but is substantially free of any pharmaceutically active agent. The core is "substantially free" of any drug in that minor, trivial amounts of drug can be present in the tablet core in less preferred embodiments, but significant or therapeutic amounts of drug are not present in the core. Such trivial amounts of active agent are generally 5% or less and typically 1% or less of the total amount of active agent contained in the tablet. For example, in a tablet having a 1 mg strength, a core containing 0.05 mg of the drug is considered to be substantially free of the drug. But this is not preferred. Instead, the tablets of the invention preferably contain no drug or pharmaceutically active agent in the core; i.e., no drug is intentionally placed within the tablet core. For clarity, the limitation of "no drug" in the core is not meant to exclude tablets where accidental and/or trace amounts of drug migrate from the outer compression coating layer to the inner tablet core or its boundary layer such as during compression or even during storage. Rather, the point is that no drug was used to create the core and hence it is considered to be drug free and to contain no pharmaceutically active agent.

The tablet core is a small tablet having a size generally in the range of 3 to 7 mm, typically 5 or 6 mm. The excipient(s) used in the tablet core are not particularly limited and generally include any binder, diluent, and/or filler and optionally a lubricant. The tablet core may be coated, e.g., film coated, etc., but such is typically not necessary or desired as the outer compression coating layer is normally applied without an intermediate coating or boundary between the tablet core and compression coating.

In many embodiments it is desirable to have a matrix forming composition in the tablet core, even though no drug will be dispersed therein. The tablet core matrix can be the same or different type (e.g., lipophilic rather than hydrophilic) than used in the outer compression coating layer. Usually, however, the matrix in the tablet core and outer compression coating are of the same type and thus are both typically water-swellable matrices. In either event, the tablet core typically contains a pH-insensitive swellable hydrophilic polymer optionally in combination with a water-sensitive swellable hydrophilic polymer, such as those described above. The matrix composition is typically in addition to a binder, filler and/or diluent.

More specifically, the above descriptions of the composition of the outer compression coating layer are equally applicable to describing the compositions of the inner tablet core, with the exception that the drug is not present in the tablet core. For example, an inner tablet core can comprise a water-swellable matrix comprising (i) at least one pH-sensitive swellable hydrophilic polymer, which is a cross-linked polyacrylic acid polymer, and (ii) at least one pH-insensitive swellable hydrophilic polymer; and optionally a water insoluble binder. These excipients can be the same as or different from the species selected for the outer compression coating layer; i.e., two different grades of HPMC; or HPMC in compression coating but kollidon SR in inner tablet core as the pH-insensitive hydrophilic polymers. In a preferred embodiment, each excipient present, in an amount of at least 1%, in the outer compression coating layer is also present in the inner tablet core; more preferably present in the same mass ratios +/−10%.

The mass ratio between the inner tablet core and the outer compression coating layer is typically 1 to $\geq 2$, respectively. Depending on the composition, tabletting issues such as capping may be too problematic at weight ratios of 1 to less than 2 (core to coating). Higher weight ratios of outer compression coating layer are generally less problematic and typically can range up to 1:10, with a common range being 1:2-8. A preferred ratio range of tablet core to outer compression coating layer, especially for the preferred two component water-swellable matrix formulations, is 15:85 to 30:70 (core to compression coating, respectively).

From a practical standpoint, the compression coating should add at least 2 mm to the overall size of the inner core tablet, i.e., compression coating layer having at least about 1 mm in thickness all around the inner tablet core, and frequently adding 3 to 4 mm in size (i.e., 1.5 to 2 mm coating thickness). The overall tablet size is specified instead of the thickness of the outer compression coating layer because of ease of measurement and to eliminate any uncertainty in the event that the coating thickness varies. Thus, the total tablet size is typically 8 to 12 mm, with 9 and 10 mm being the most common. Round is the typical tablet shape; e.g., the inner tablet core being made from a flat round punch and the outer compression coating layer using a round convex punch. In principle, however, other shapes such as oval are also possible.

The overall mass of the tablet is generally from 100 to 500 mg, preferably from 200 to 400 mg. The tablets preferably exhibit hardness from about 40 to about 180 N, typically from 120-150 N.

By selecting the water-swellable matrix-forming polymeric components, including the polymer species and their relative amounts, as well as the overall amount of the matrix-forming composition in the tablet, the controlled release of the drug can be manipulated to a desired release profile. As stated above, the tablet preferably exhibits a dissolution profile wherein 95% of drug is release in not less than 12 hours, more typically not less than 14 hours, and in some preferred embodiments not less than 16 hours, as measured in an appropriate or FDA-approved dissolution test/conditions (defined hereinafter).

To provide a tablet that releases tamsulosin for a long time and preferably even in the colon, the tablet should typically have an in vitro dissolution profile such that tamsulosin is still being released after 18 hours. That is, less than 100% of the tamsulosin is released at 18 hours, preferably no more than 97%, more preferably not more than 95% is released at 18 hours, using an appropriate dissolution; e.g., an in vitro dissolution test conducted under appropriate conditions. Appropriate conditions for a dissolution test are routinely determined by workers of ordinary skill in the art for a given tablet. A dissolution test described in a new (or abbreviated new) drug application for a tamsulosin tablet, for example, that a regulatory authority such as the U.S. FDA finds acceptable is an example of a dissolution test performed under "appropriate" conditions (hereinafter an "FDA-approved test"). Using an FDA-approved test is a preferred "appropriate" set of conditions for determining the dissolution profile and for determining whether the above-described profile is met. The testing is performed in conventional Ph. Eur. or USP apparatus. That a tablet has not finished releasing the tamsulosin at 18 hours, but rather is still releasing tamsulosin, is a good indication that in vivo the tamsulosin will be released throughout the digestive tract, including the colon.

In general, the tamsulosin tablets of the invention typically meet the following dissolution criteria when subjected to a dissolution test under appropriate conditions: less than 40% of tamsulosin is released within 2 hours; less than 60% is released in 6 hours; and less than 80% is released in 10 hours. Preferably the dissolution curve or profile is such that less than 80% is released in 12 hours. Typically the dissolution media in an appropriate dissolution test is a phosphate buffer or other simulated intestinal fluid at pH 6.8. The testing is performed in conventional Ph. Eur. or USP apparatus, by a paddle or a basket method using conventional rotation speeds. In one embodiment the testing is performed in a single dissolution medium of simulated intestinal fluid (pH 6.8) by a paddle method, preferably at 50 rpm. The use of so-called Japanese basket may also be used. A two step dissolution media test may also be appropriate wherein the tablets are first immersed for 2 hours in simulated gastric fluid (typically without enzymes as is common in the art), and afterwards in phosphate buffer of pH 6.8 to simulate intestinal fluid. For clarity, it is not necessary that the preferred tablets achieve the recited dissolution release rates in every appropriate dissolution test, but rather that they achieve such release in at least one appropriate dissolution testing condition.

In a preferred embodiment, the tamsulosin tablets of the present invention do not exhibit a food effect. That is, the tablets can be administered to a patient in either a fasted or a fed state without significantly affecting the release/bioavailability of the tamsulosin.

The controlled release tablets of the present invention can be made by known methods and techniques in the art. Generally, the inner tablet core is made by any conventional tabletting including wet granulation, direct compression, etc. Direct compression is particularly favored. The components of the inner tablet core, including a lubricant and glidant, are blended and dosed onto a tablet punch of a proper shape and size, e.g., round diameter 5-6 mm, and compressed to form a tablet. This tablet forms the inner tablet core of the final tablet-in-tablet. The tablet may be allowed to age before being used in the subsequent compression coating step in order to ensure volume equilibration is reached.

A second, larger tablet punch, e.g. round diameter 10 mm, is partially charged with a small amount of a powder blend made from the outer compression coating layer-forming ingredients. The previously produced tablet core is placed and centered in the partially charged punch, additional coating layer powder blend is added, and the whole material compressed to form a compression coating layer around the tablet core; e.g. a tablet-in-tablet. Tablet presses allowing such a technique are known as alternate tablet presses or "tablet-in tablet" presses and are known in the art.

In an advantageous process of making the composition of the outer layer, (partial) wet granulation is used to form a granulate of the active before making the final blend of the outer layer composition. For example, in making a tamsulosin tablet, the tamsulosin or its salt and a binder (50-100% of the amount, which will be present in the final composition) are wet granulated to form a granulate. The granulate can contain additional excipients and typically contains a small amount (e.g. 1-10%) of the pH-insensitive swellable hydrophilic polymer discussed above. A typical granulate would thus comprise at least 70%, typically 80%, and more typically at least 90% of water-insoluble binder. A suitable liquid medium for wet granulation is water, which is substantially removed from the granulate and/or from the subsequent blend by conventional drying before tabletting/compression. The granulate is then dry mixed with the pH-insensitive swellable hydrophilic polymer, or the remainder thereof, and the pH-sensitive swellable hydrophilic polymer discussed above, in one or more steps to form a tablet blend. Additional excipients such as a lubricant, etc., are typically also included in the tablet blend and are added together with, or separately from, the matrix-forming polymers in the same or different mixing steps. Generally no additional active is added; i.e. no extra-granular tamsulosin or salt thereof. Binder, however, can be further added, i.e., both intra-granular and extra-granular binder can be present in the tablet. Typically most or all of the binder is intra-granular, e.g., at least 60% and generally 70% to 95%.

The partial wet granulation technique can improve content uniformity between tablets which can be a concern as the relative amount of tamsulosin drug becomes very small; e.g., low doses of tamsulosin in larger tablets.

The tablets may be used to deliver the drug incorporated therein in a once daily dosing regimen. The tamsulosin tablets of the invention in particular are useful in treatment of tamsulosin-treatable diseases, especially BPH, in dosages and regimens similar to the marketed tamsulosin-OCAS tablets. The invention is further illustrated by the following non-limiting examples.

EXAMPLE 1

Composition

|  | mg | % wrt total | mg | % wrt total |
|---|---|---|---|---|
| Inner core |  |  |  |  |
| HPMC K100MCR | 36 | 15.0 | 36 | 12.0 |
| MCC PH102 | 20.37 | 8.5 | 20.37 | 6.8 |
| Carbomer 71GNF | 3 | 1.2 | 3 | 1.0 |
| Silica dioxide 200 VV | 0.3 | 0.1 | 0.3 | 0.1 |
| iron oxide red | 0.03 | 0.01 | 0.03 | 0.01 |
| Mg stearate | 0.3 | 0.1 | 0.3 | 0.1 |
| Outer core |  |  |  |  |
| R-tamsulosin•HCl | 0.4 | 0.2 | 0.4 | 0.1 |
| MCC PH101 | 60.8 | 25.3 | 81.2 | 27.1 |
| HPMC K100MCR | 108 | 45.0 | 144 | 48.0 |
| Carbomer 71GNF | 9 | 3.7 | 12 | 4.0 |
| Silica dioxide 200 VV | 0.9 | 0.4 | 1.2 | 0.4 |
| Mg stearate | 0.9 | 0.4 | 1.2 | 0.4 |
| Total mass | 240 | 100 | 300 | 100 |

Manufacturing Process

The preparation of the cores was as follows: iron oxide was sieved over a 180 micron sieve. A bit of HPMC was premixed with silica, and sieved over a 1.0 mm sieve. MCC, HPMC, carbomer, iron oxide and silica were mixed in a free fall mixer for 20 minutes. Mg stearate was sieved over a 850 micron sieve and added to the blend. The blend was mixed for an additional 5 minutes. The blend was compressed into 60 mg tablets with a diameter of 6 mm.

The wet granulation process was performed as follows: Tamsulosin salt and MCC were granulated in a high shear granulator with 755 gram water (1500 gram granulation scale). The tamsulosin and MCC were mixed for 10 minutes. Water was added in 17 minutes with an impeller speed of 235 rpm and a chopper speed of 1500 rpm. The granulate was dried overnight in an oven with an inlet temperature of 40° C. The dried granulate was sieved over a 500 micron sieve. Half of the HPMC was added to the blend and this was mixed for 15 minutes. The remaining HPMC was added and the blend was mixed for another 10 minutes. A preblend of a bit of HPMC and silica was made, and this preblend was sieved over a 1.0 mm sieve. The preblend and the carbomer were added to the blend and mixed for 15 minutes. Magnesium stearate was sieved over a 0.85 mm sieve, added to the blend and the blend was mixed for another 5 minutes. The blend and the cores were used to compress tablet-in-tablets with a 240 mg total tablet mass and a diameter of 10 mm.

The blend of the shell could also be prepared with a direct compression process. The process would then be as follows: tamsulosin and a part of the HPMC (TSL:HPMC, 1:20) were mixed for 5 minutes in a free fall mixer and sieved over a 0.3 mm sieve. Than 50% of the total HPMC was added to the blend and it was mixed for another 10 minutes in a free fall mixer. The remaining HPMC was added and the blend was mixed for another 10 minutes. The MCC, silica (pre-blended with a bit of HPMC and sieved over a 1.0 mm sieve) and carbomer were added and the blend was mixed for another 15 minutes. Magnesium stearate was sieved through a 0.8 mm sieve and added to the blend. The blend and the cores were used to compress tablet-in-tablets with a 240 mg total tablet mass and a diameter of 10 mm.

By analogous methods, the 300 mg total weight tablets can also be made.

EXAMPLE 2

|  | % | mg/tablet |
|---|---|---|
| Inner core |  |  |
| MCC PH 102 | 33.95 | 20.37 |
| iron oxide red | 0.05 | 0.03 |
| HPMC K100M CR | 60 | 36 |
| Carbomer 71GNF | 5 | 3 |
| Silica dioxide 200 VV | 0.5 | 0.3 |
| Magnesium stearate | 0.5 | 0.3 |
| Tablet mass (mg) | 100 | 60 |
| Outer core Intra granular |  |  |
| R-Tamsulosin HCl | 0.21 | 0.4 |
| MCC PH 101 | 33.79 | 64.2 |
| Extra granular |  |  |
| HPMC K100M CR | 60 | 114 |
| Carbomer 71GNF | 5 | 9.5 |
| Silica dioxide 200 VV | 0.5 | 0.95 |
| Magnesium stearate | 0.5 | 0.95 |
| Tablet mass (mg) | 100 | 190 |
| Total tablet mass (mg) |  | 250 |

The preparation of the cores was as follows; MCC, HPMC, carbomer, iron oxide and silica were sieved over a 1 mm sieve. The excipients were mixed in a free fall mixer for 20 minutes. Magnesium stearate was sieved over a 0.8 mm sieve and added to the blend. The blend was mixed for another 5 minutes. The blend was compressed into 60 mg tablets with a diameter of 5 mm.

TSL and MCC were mixed in a high shear granulator, while water was added. The obtained wet mass was dried in an oven until a LOD of 3.3% was reached. The dry granulate was force sieved over a 500 micron sieve. All excipients, except magnesium stearate, were sieved over a 1.0 mm sieve. The half of the HPMC was added to the blend and the blend was mixed for 15 minutes in a free fall mixer. The remaining HPMC was added and the blend was mixed for another 10 minutes. The silica and the carbomer were added to the blend and mixed for 15 minutes at 22 rpm. Magnesium stearate was sieved over a 0.8 mm sieve, added to the blend and the blend was mixed for another 5 minutes.

Tablets of 9 mm were compressed with the tablet in tablet machine.

EXAMPLE 3

|  | % | mg/tablet |
|---|---|---|
| Inner core |  |  |
| MCC PH 102 | 33.95 | 20.37 |
| iron oxide red | 0.05 | 0.03 |
| HPMC K100M CR | 60 | 36 |
| Carbomer 71GNF | 5 | 3 |
| Silica dioxide 200 VV | 0.5 | 0.3 |
| Magnesium stearate | 0.5 | 0.3 |
| Tablet mass (mg) | 100 | 60 |
| Outer core Intra granular |  |  |
| R-Tamsulosin HCl | 0.18 | 0.4 |
| MCC PH 101 | 33.82 | 74.4 |
| Extra granular |  |  |
| HPMC K100M CR | 60 | 132 |
| Carbomer 71GNF | 5 | 11 |
| Silica dioxide 200 VV | 0.5 | 1.1 |
| Magnesium stearate | 0.5 | 1.1 |
| Tablet mass (mg) | 100 | 220 |
| Total tablet mass (mg) |  | 280 |

The preparation of the cores was as follows; MCC, HPMC, carbomer, iron oxide and silica were sieved over a 1 mm sieve. The excipients were mixed in a free fall mixer for 20 minutes. Magnesium stearate was sieved over a 0.8 mm sieve and added to the blend. The blend was mixed for another 5 minutes. The blend was compressed into 60 mg tablets with a diameter of 6 mm.

TSL and MCC were mixed in a high shear granulator, while water was added. The obtained wet mass was dried in an oven until a LOD of 3.2% was reached. The dry granulate was force sieved over a 500 micron sieve. All excipients, except magnesium stearate, were sieved over a 1.0 mm sieve. The half of the HPMC was added to the blend and the blend was mixed for 15 minutes in a free fall mixer. The remaining HPMC was added and the blend was mixed for another 10 minutes. The silica and the carbomer were added to the blend and mixed for 15 minutes at 22 rpm. Magnesium stearate was sieved over a 0.8 mm sieve, added to the blend and the blend was mixed for another 5 minutes.

Tablets of 10 mm were compressed on a killian tablet-in-tablet press.

EXAMPLE 4

|  | % | mg/tablet |
|---|---|---|
| Inner core |  |  |
| MCC PH 102 | 33.95 | 20.37 |
| iron oxide red | 0.05 | 0.03 |
| HPMC K100M CR | 60 | 36 |
| Carbomer 71GNF | 5 | 3 |
| Silica dioxide 200 VV | 0.5 | 0.3 |
| Magnesium stearate | 0.5 | 0.3 |
| Tablet mass (mg) | 100 | 60 |
| Outer core Intra granular |  |  |
| R-Tamsulosin HCl | 0.19 | 0.4 |
| MCC PH 101 | 33.81 | 71 |
| Extra granular |  |  |
| HPMC K100M CR | 60.25 | 126.525 |
| Carbomer 71GNF | 5 | 10.5 |

-continued

|  | % | mg/tablet |
|---|---|---|
| Silica dioxide 200 VV | 0.5 | 1.05 |
| Magnesium stearate | 0.25 | 0.525 |
| Tablet mass (mg) | 100 | 210 |
| Total tablet mass (mg) |  | 270 |

The preparation of the cores was as follows; MCC, HPMC, carbomer, iron oxide and silica were sieved over a 1 mm sieve. The excipients were mixed in a free fall mixer for 20 minutes. Magnesium stearate was sieved over a 0.8 mm sieve and added to the blend. The blend was mixed for another 5 minutes. The blend was compressed into 60 mg tablets with a diameter of 5 mm.

TSL and MCC were mixed in a high shear granulator, while water was added. The obtained wet mass was dried in an oven until a LOD of 2.5% was reached. The dry granulate was force sieved over a 500 micron sieve. All excipients, except magnesium stearate, were sieved over a 1.0 mm sieve. HPMC with an LOD of 0.5% was used. The half of the HPMC was added to the blend and the blend was mixed for 15 minutes in a free fall mixer. The remaining HPMC was added and the blend was mixed for another 10 minutes. The silica and the carbomer were added to the blend and mixed for 15 minutes at 22 rpm. Magnesium stearate was sieved over a 0.8 mm sieve, added to the blend and the blend was mixed for another 5 minutes.

Tablets of 9 mm were compressed on a killian tablet-in-tablet press.

EXAMPLE 5

|  | % | mg/tablet |
|---|---|---|
| Inner core |  |  |
| MCC PH 102 | 33.95 | 20.37 |
| iron oxide red | 0.05 | 0.03 |
| HPMC K100M CR | 60 | 36 |
| Carbomer 71GNF | 5 | 3 |
| Silica dioxide 200 VV | 0.5 | 0.3 |
| Magnesium stearate | 0.5 | 0.3 |
| Tablet mass (mg) | 100 | 60 |
| Outer core |  |  |
| Intra granular |  |  |
| R-Tamsulosin HCl | 0.19 | 0.4 |
| MCC PH 101 | 33.81 | 71 |
| Extra granular |  |  |
| HPMC K100M CR | 60 | 126 |
| Carbomer 71GNF | 5 | 10.5 |
| Silica dioxide 200 VV | 0.5 | 1.05 |
| Magnesium stearate | 0.5 | 1.05 |
| Tablet mass (mg) | 100 | 210 |
| Total tablet mass (mg) |  | 270 |

The preparation of the cores was as follows; MCC, HPMC, carbomer, iron oxide and silica were sieved over a 1 mm sieve. The excipients were mixed in a free fall mixer for 20 minutes. Magnesium stearate was sieved over a 0.8 mm sieve and added to the blend. The blend was mixed for another 5 minutes. The blend was compressed into 60 mg tablets with a diameter of 5 mm.

TSL and MCC were mixed in a high shear granulator, while water was added. The obtained wet mass was dried in an oven until a LOD of 4.0% was reached. The dry granulate was force sieved over a 500 micron sieve. All excipients, except magnesium stearate, were sieved over a 1.0 mm sieve. The half of the HPMC was added to the blend and the blend was mixed for 15 minutes in a free fall mixer. The remaining HPMC was added and the blend was mixed for another 10 minutes. The silica and the carbomer were added to the blend and mixed for 15 minutes at 22 rpm. Magnesium stearate was sieved over a 0.8 mm sieve, added to the blend and the blend was mixed for another 5 minutes.

Tablets of 9 mm were compressed on a killian tablet-in-tablet press.

EXAMPLE 6

|  | % | mg/tablet |
|---|---|---|
| Inner core |  |  |
| MCC PH 102 | 33.95 | 20.37 |
| iron oxide red | 0.05 | 0.03 |
| HPMC K100M CR | 60 | 36 |
| Carbomer 71GNF | 5 | 3 |
| Silica dioxide 200 VV | 0.5 | 0.3 |
| Magnesium stearate | 0.5 | 0.3 |
| Tablet mass (mg) | 100 | 60 |
| Outer core |  |  |
| Intra granular |  |  |
| R-Tamsulosin HCl | 0.19 | 0.4 |
| MCC PH 101 | 33.81 | 71 |
| Extra granular |  |  |
| HPMC K100M CR | 60.4 | 126.84 |
| Carbomer 71GNF | 5 | 10.5 |
| Silica dioxide 200 VV | 0.5 | 1.05 |
| Magnesium stearate | 0.1 | 0.21 |
| Tablet mass (mg) | 100 | 210 |
| Total tablet mass (mg) |  | 270 |

The preparation of the cores was as follows; MCC, HPMC, carbomer, iron oxide and silica were sieved over a 1 mm sieve. The excipients were mixed in a free fall mixer for 20 minutes. Magnesium stearate was sieved over a 0.8 mm sieve and added to the blend. The blend was mixed for another 5 minutes. The blend was compressed into 60 mg tablets with a diameter of 5 mm.

TSL and MCC were mixed in a high shear granulator, while water was added. The obtained wet mass was dried in an oven until a LOD of 3.8% was reached. The dry granulate was force sieved over a 500 micron sieve. All excipients, except magnesium stearate, were sieved over a 1.0 mm sieve. The half of the HPMC was added to the blend and the blend was mixed for 15 minutes in a free fall mixer. The remaining HPMC was added and the blend was mixed for another 10 minutes. The silica and the carbomer were added to the blend and mixed for 15 minutes at 22 rpm. Magnesium stearate was sieved over a 0.8 mm sieve, added to the blend and the blend was mixed for another 5 minutes.

Tablets of 9 mm were compressed on a killian tablet-in-tablet press.

EXAMPLE 7

|  | % | mg/tablet |
|---|---|---|
| Inner core |  |  |
| MCC PH 102 | 33.95 | 20.37 |
| iron oxide red | 0.05 | 0.03 |
| HPMC K100M CR | 60 | 36 |
| Carbomer 71GNF | 5 | 3 |
| Silica dioxide 200 VV | 0.5 | 0.3 |
| Magnesium stearate | 0.5 | 0.3 |
| Tablet mass (mg) | 100 | 60 |
| Outer core |  |  |
| Intra granular |  |  |
| R-Tamsulosin HCl | 0.2 | 0.4 |
| MCC PH 101 | 33.8 | 67.6 |
| Extra granular |  |  |
| HPMC K100M CR | 60 | 120 |
| Carbomer 71GNF | 5 | 10 |
| Silica dioxide 200 VV | 0.5 | 1.0 |
| Magnesium stearate | 0.5 | 1.0 |
| Tablet mass (mg) | 100 | 200 |
| Total tablet mass (mg) |  | 260 |

The preparation of the cores was as follows; MCC, HPMC, carbomer, iron oxide and silica were sieved over a 1 mm sieve. The excipients were mixed in a free fall mixer for 20 minutes. Magnesium stearate was sieved over a 0.8 mm sieve and added to the blend. The blend was mixed for another 5 minutes. The blend was compressed into 60 mg tablets with a diameter of 6 mm.

TSL and MCC were mixed in a high shear granulator, while water was added. The obtained wet mass mass was dried in an oven until a LOD of 3.3% was reached. The dry granulate was force sieved over a 500 micron sieve. All excipients, except magnesium stearate, were sieved over a 1.0 mm sieve. The half of the HPMC was added to the blend and the blend was mixed for 15 minutes in a free fall mixer. The remaining HPMC was added and the blend was mixed for another 10 minutes. The silica and the carbomer were added to the blend and mixed for 15 minutes at 22 rpm. Magnesium stearate was sieved over a 0.8 mm sieve, added to the blend and the blend was mixed for another 5 minutes.

Tablets of 10 mm were compressed on a killian tablet-in-tablet press.

EXAMPLE 8

|  | % | mg/tablet |
|---|---|---|
| Inner core |  |  |
| MCC PH 102 | 33.95 | 20.37 |
| iron oxide red | 0.05 | 0.03 |
| HPMC K100M CR | 60 | 36 |
| Carbomer 71GNF | 5 | 3 |

-continued

|  | % | mg/tablet |
|---|---|---|
| Silica dioxide 200 VV | 0.5 | 0.3 |
| Magnesium stearate | 0.5 | 0.3 |
| Tablet mass (mg) | 100 | 60 |
| Outer core |  |  |
| Intra granular |  |  |
| R-Tamsulosin HCl | 0.19 | 0.4 |
| MCC PH 101 | 33.81 | 71 |
| Extra granular |  |  |
| HPMC K100M CR | 60.25 | 126.525 |
| Carbomer 71GNF | 5 | 10.5 |
| Silica dioxide 200 VV | 0.5 | 1.05 |
| Magnesium stearate | 0.25 | 0.525 |
| Tablet mass (mg) | 100 | 210 |
| Total tablet mass (mg) |  | 270 |

The preparation of the cores was as follows; MCC, HPMC, carbomer, iron oxide and silica were sieved over a 1 mm sieve. The excipients were mixed in a free fall mixer for 20 minutes. Magnesium stearate was sieved over a 0.8 mm sieve and added to the blend. The blend was mixed for another 5 minutes. The blend was compressed into 60 mg tablets with a diameter of 5 mm.

TSL and MCC were mixed in a high shear granulator, while water was added. The obtained wet mass was dried in an oven until a LOD of 2.5% was reached. The dry granulate was force sieved over a 500 micron sieve. All excipients, except magnesium stearate, were sieved over a 1.0 mm sieve. The half of the HPMC was added to the blend and the blend was mixed for 15 minutes in a free fall mixer. The remaining HPMC was added and the blend was mixed for another 10 minutes. The silica and the carbomer were added to the blend and mixed for 15 minutes at 22 rpm. Magnesium stearate was sieved over a 0.8 mm sieve, added to the blend and the blend was mixed for another 5 minutes.

Tablets of 9 mm were compressed on a killian tablet-in-tablet press.

EXAMPLE 9

|  | % | mg/tablet |
|---|---|---|
| Inner core |  |  |
| MCC PH 102 | 33.95 | 20.37 |
| iron oxide red | 0.05 | 0.03 |
| HPMC K100M CR | 60 | 36 |
| Carbomer 71GNF | 5 | 3 |
| Silica dioxide 200 VV | 0.5 | 0.3 |
| Magnesium stearate | 0.5 | 0.3 |
| Tablet mass (mg) | 100 | 60 |
| Outer core |  |  |
| Intra granular |  |  |
| R-Tamsulosin HCl | 0.19 | 0.4 |
| MCC PH 101 | 33.81 | 71 |
| Extra granular |  |  |
| HPMC K100M CR | 60 | 126 |
| Carbomer 71GNF | 5 | 10.5 |

-continued

|  | % | mg/tablet |
|---|---|---|
| Silica dioxide 200 VV | 0.5 | 1.05 |
| Magnesium stearate | 0.5 | 1.05 |
| Tablet mass (mg) | 100 | 210 |
| Total tablet mass (mg) |  | 270 |

The preparation of the cores was as follows; MCC, HPMC, carbomer, iron oxide and silica were sieved over a 1 mm sieve. The excipients were mixed in a free fall mixer for 20 minutes. Magnesium stearate was sieved over a 0.8 mm sieve and added to the blend. The blend was mixed for another 5 minutes. The blend was compressed into 60 mg tablets with a diameter of 5 mm.

TSL and MCC were mixed in a high shear granulator, while water was added. The obtained wet mass was dried in an oven until a LOD of 3.6% was reached. The dry granulate was forced sieved over a 500 micron sieve. All excipients, except magnesium stearate, were sieved over a 1.0 mm sieve. The half of the HPMC was added to the blend and the blend was mixed for 15 minutes in a free fall mixer. The remaining HPMC was added and the blend was mixed for another 10 minutes. The silica and the carbomer were added to the blend and mixed for 15 minutes at 22 rpm. Magnesium stearate was sieved over a 0.8 mm sieve, added to the blend and the blend was mixed for another 5 minutes.

Tablets of 9 mm were compressed on a killian tablet-in-tablet press.

EXAMPLE 10

|  | % | mg/tablet |
|---|---|---|
| Inner core |  |  |
| MCC PH 102 | 33.95 | 20.37 |
| iron oxide red | 0.05 | 0.03 |
| HPMC K100M CR | 60 | 36 |
| Carbomer 71GNF | 5 | 3 |
| Silica dioxide 200 VV | 0.5 | 0.3 |
| Magnesium stearate | 0.5 | 0.3 |
| Tablet mass (mg) | 100 | 60 |
| Outer core |  |  |
| Intra granular |  |  |
| R-Tamsulosin HCl | 0.19 | 0.4 |
| MCC PH 101 | 33.81 | 71 |
| Extra granular |  |  |
| HPMC K100M CR | 60 | 126 |
| Carbomer 71GNF | 5 | 10.5 |
| Silica dioxide 200 VV | 0.5 | 1.05 |
| Magnesium stearate | 0.5 | 1.05 |
| Tablet mass (mg) | 100 | 210 |
| Total tablet mass (mg) |  | 270 |

The preparation of the cores was as follows; MCC, HPMC, carbomer, iron oxide and silica were sieved over a 1 mm sieve. The excipients were mixed in a free fall mixer for 20 minutes. Magnesium stearate was sieved over a 0.8 mm sieve and added to the blend. The blend was mixed for another 5 minutes. The blend was compressed into 60 mg tablets with a diameter of 5 mm.

TSL and MCC were mixed in a high shear granulator, while water was added. The obtained wet mass was dried in an oven until a LOD of 6.2% was reached. The dry granulate was force sieved over a 500 micron sieve. All excipients, except magnesium stearate, were sieved over a 1.0 mm sieve. The half of the HPMC was added to the blend and the blend was mixed for 15 minutes in a free fall mixer. The remaining HPMC was added and the blend was mixed for another 10 minutes. The silica and the carbomer were added to the blend and mixed for 15 minutes at 22 rpm. Magnesium stearate was sieved over a 0.8 mm sieve, added to the blend and the blend was mixed for another 5 minutes.

Tablets of 9 mm were compressed on a killian tablet-in-tablet press.

Each of the patents, patent applications, and journal articles mentioned above are incorporated herein by reference. The invention having been described it will be obvious that the same may be varied in many ways and all such modifications are contemplated as being within the scope of the invention as defined by the following claims.

We claim:

1. A controlled release pharmaceutical tablet, comprising:
   (a) an inner tablet core having a size within the range of 3 to 7 mm and comprising at least one pharmaceutically acceptable excipient but substantially free from any pharmaceutically active agent; and
   (b) an outer compression coating layer surrounding said inner tablet core and which comprises a controlled release matrix having a pharmaceutically active agent dispersed therein;
   wherein the total amount of pharmaceutically active agent contained in said tablet is within the range of 0.1 to 5 mg.

2. The pharmaceutical tablet according to claim 1, wherein said inner tablet core contains no pharmaceutical active agent.

3. The pharmaceutical tablet according to claim 2, wherein said outer compression coating layer adds at least 2 mm to the total controlled release tablet size.

4. The pharmaceutical tablet according to claim 3, wherein said pharmaceutical active agent is tamsulosin or a pharmaceutically acceptable salt thereof.

5. A controlled release tamsulosin tablet comprising:
   (a) an inner tablet core having a size within the range of 3 to 7 mm and comprising at least one pharmaceutically acceptable excipient and substantially free from any pharmaceutically active agent; and
   (b) an outer compression coating layer surrounding said inner tablet core and which comprises 0.1 to 2 mg of tamsulosin or salt thereof dispersed in a water-swellable matrix comprising (i) at least one pH-sensitive swellable hydrophilic polymer, which is a cross-linked polyacrylic acid polymer, and (ii) at least one pH-insensitive swellable hydrophilic polymer; and optionally a water insoluble binder.

6. The tamsulosin tablet according to claim 5, wherein said inner tablet core contains no pharmaceutical active agent.

7. The tamsulosin tablet according to claim 6, wherein said tamsulosin is tamsulosin hydrochloride.

8. The tamsulosin tablet according to claim 6, wherein said tamsulosin or salt thereof is contained in an amount between 0.1 to 1 mg.

9. The tamsulosin tablet according to claim 6, wherein said pH-insensitive polymer is a linear polymer.

10. The tamsulosin tablet according to claim 6, wherein said pH-sensitive polymer is a carbomer.

11. The tamsulosin tablet according to claim 10, wherein said pH-insensitive polymer is a hydroxypropyl methylcellulose.

12. The tamsulosin tablet according to claim 11, wherein said hydroxypropyl methylcellulose has a nominal dynamic viscosity of at least about 100,000 mPa/s.

13. The tamsulosin tablet according to claim 6, wherein said outer compression coating layer contains a water insoluble binder.

14. The tamsulosin tablet according to claim 13, wherein said water insoluble binder is microcrystalline cellulose.

15. The tamsulosin tablet according to claim 6, wherein said inner tablet core has a diameter of 5-6 mm.

16. The tamsulosin tablet according to claim 6, wherein said at least one excipient in said inner tablet core comprises a water-swellable matrix composition and optionally a water insoluble binder.

17. The tamsulosin tablet according to claim 11, wherein said at least one excipient in said inner tablet core comprises a water-swellable matrix composition and optionally a water insoluble binder.

18. The tamsulosin tablet according to claim 17, wherein said water-swellable matrix composition of said inner tablet core comprises at least one pH-sensitive swellable hydrophilic polymer, which is a cross-linked polyacrylic acid polymer, and at least one pH-insensitive swellable hydrophilic polymer.

19. The tamsulosin tablet according to claim 18, wherein said inner tablet core contains a water insoluble binder and wherein said water insoluble binder is microcrystalline cellulose.

20. The tamsulosin tablet according to claim 6, wherein said inner tablet core and said outer compression coating layer contain the same water-swellable matrix composition and water insoluble binder in the same mass ratios +/−10%.

21. The tamsulosin tablet according to claim 6, wherein the mass ratio of said inner tablet core to said outer compression coating layer is from 15:85 to 30:70, respectively.

22. The tamsulosin tablet according to claim 6, wherein said tamsulosin tablet exhibits an in vitro dissolution profile such that said tamsulosin is still being released after 18 hours in artificial intestinal fluid.

* * * * *